(12) United States Patent
Bradley et al.

(10) Patent No.: US 7,181,975 B1
(45) Date of Patent: Feb. 27, 2007

(54) WIRELESS CAPACITANCE PRESSURE SENSOR

(75) Inventors: Alistair D. Bradley, Edinburgh (GB); Stephen R. Shiffer, Xenia, OH (US)

(73) Assignee: Honeywell International, Morristown, NJ (US)

( * ) Notice: Subject to any disclaimer, the term of this patent is extended or adjusted under 35 U.S.C. 154(b) by 0 days.

(21) Appl. No.: 11/226,085

(22) Filed: Sep. 13, 2005

(51) Int. Cl.
*G01L 9/12* (2006.01)

(52) U.S. Cl. .......................... 73/724; 73/715; 73/718; 361/283.1

(58) Field of Classification Search .......... 73/700–756; 361/283.1–283.4
See application file for complete search history.

(56) References Cited

U.S. PATENT DOCUMENTS

| | | | | |
|---|---|---|---|---|
| 4,903,532 A | * | 2/1990 | Tamai et al. | 73/718 |
| 5,479,827 A | * | 1/1996 | Kimura et al. | 73/718 |
| 6,019,002 A | * | 2/2000 | Lee | 73/724 |
| 6,150,681 A | * | 11/2000 | Allen | 257/254 |
| 6,179,586 B1 | | 1/2001 | Herb et al. | 417/480 |
| 6,205,861 B1 | * | 3/2001 | Lee | 73/724 |
| 6,460,234 B1 | * | 10/2002 | Gianchandani | 29/25.35 |
| 6,470,754 B1 | * | 10/2002 | Gianchandani | 73/718 |
| 6,532,834 B1 | * | 3/2003 | Pinto et al. | 73/862.626 |
| 6,658,938 B2 | * | 12/2003 | McIntosh | 73/514.32 |
| 6,789,429 B2 | * | 9/2004 | Pinto et al. | 73/718 |
| 6,901,807 B1 | | 6/2005 | Wang et al. | 73/718 |

* cited by examiner

*Primary Examiner*—Edward Lefkowitz
*Assistant Examiner*—Jermaine Jenkins
(74) *Attorney, Agent, or Firm*—Matthew F. Lambrinos; Kermit D. Lopez; Luis M. Ortiz

(57) ABSTRACT

A wireless pressure sensor system has a pressure sensing capacitor and an inductor mounted on a common housing. The pressure sensing capacitor has a conductive diaphragm, a dielectric layer and a fixed electrode separated at least in part from the diaphragm by a gap formed in the housing. The electrode is arranged with a protrusion such that displacement of the diaphragm varies the area of capacitive contact with the electrode by rolling along the protrusion. The inductor coil and pressure sensing capacitor are connected to form a passive inductive-capacitive (LC) tank circuit. A remote interrogation circuit, inductively coupled to the pressure sensor inductor coil can be utilized to detect the resonant frequency of the LC tank which varies as a function of pressure sensed by the diaphragm.

19 Claims, 6 Drawing Sheets

WIRELESS CAPACITANCE PRESSURE SENSOR

TECHNICAL FIELD

Embodiments are generally related to sensors and applications and, more particularly, to pressure sensors. Embodiments are additionally related to disposable pressure sensors and wireless sensors for remotely sensing pressure. Additionally, embodiments are related to low cost pressure sensors for applications such as medical apparatus.

BACKGROUND

Many different techniques have been proposed for sensing the pressure and/or temperature in catheters and fluid cartridges, and for delivering this information to an operator so that he or she is aware of pressure and temperature conditions associated with a catheter or a cartridge and any fluid, such as blood flowing therein.

In medical apparatus, as well as other applications, disposable sensors are required which can be implemented in a cost-effective manner. Typical pressure sensors are not particularly well suited to such applications by virtue of the relatively high number of component parts, expensive materials and/or processing requirements, and high number of manufacturing-processing steps required to produce the sensors and to integrate them into the instrumentation or apparatus of the application.

There is a continuing need to provide pressure sensors for single use/disposable pressure sensing applications, such as medical applications, which can be manufactured and integrated into apparatus more efficiently and/or at lower cost.

The embodiments disclosed herein therefore directly address the shortcomings of present pressure sensors providing a low cost disposable pressure sensor that may be suitable for many price sensitive applications.

BRIEF SUMMARY OF THE INVENTION

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole.

It is, therefore, one aspect to provide for improved pressure sensors and applications.

It is another aspect to provide for a low cost disposable pressure sensor suitable for use in medical applications, such as for example extracorporeal blood monitoring and treatment apparatus.

It is a further aspect of the present invention to provide for a method of forming a low cost pressure sensor.

The aforementioned aspects of the invention and other objectives and advantages can now be achieved as described herein.

According to one aspect, a pressure sensor system has a pressure sensing capacitor and an inductor integrated together in a housing. The pressure sensing capacitor has a diaphragm, made at least in part from a conductive material, secured in the housing, for detecting a pressure differential. Formed on the housing is an electrode at least part of which can be separated from the diaphragm by a predetermined gap formed by the housing. An insulating layer, disposed between the electrode and the diaphragm, provides a dielectric layer between the electrode and the diaphragm.

The pressure sensing capacitor together with an inductor, also formed on the housing, can be electrically connected to form an inductive-capacitive (LC) tank circuit. When an electromagnetic signal is applied to the pressure sensor, the resonant frequency of the LC tank can be detected to enable determination of changes in a pressure differential applied to the diaphragm. By forming the pressure sensing capacitor and inductor on the same housing, the number of components and manufacturing steps necessary to produce the sensor are reduced enabling a low cost wireless pressure sensor to be provided.

The electrode can be arranged such that the diaphragm can roll in physical contact with the electrode upon displacement of the diaphragm. This rolling contact varies the area of capacitor formed with only a thin layer of dielectric between and thus provides a high capacitive change relative to diaphragm displacement. The pressure sensor affords an increased capacitive response for a given diaphragm displacement in comparison to other sensors without a rolling capacitive contact design so that the sensitivity of the pressure sensor can be therefore increased.

The housing, with electrode formed thereupon can be shaped such that a portion of the electrode projects towards the diaphragm. This enables the diaphragm to roll in capacitive contact with the electrode projecting portion upon application of both positive and negative pressure differentials. The electrode projection portion can have a round or curved shape. The electrode can have an inner region and an outer region surrounding the inner region, the outer region being substantially planar and the inner region projecting towards the diaphragm such that said diaphragm can roll in capacitive contact with the inner region. The inner region of electrode can have a varying gradient or varying levels of curvature along its length, chosen to give required pressure sensitivity.

The inductor can comprise an inductor coil disposed on the housing.

First and second metal interconnects are formed on the housing for electrically connecting the inductor coil to the pressure sensing capacitor. The first metal interconnect can connect one end of the coil to the electrode and a second metal interconnect can connect the other end of the coil to the diaphragm or conducting part thereof.

The housing can be formed with a portion projecting towards the diaphragm. The electrode can be contiguous with the housing projecting portion such that the electrode projects towards the diaphragm.

The diaphragm can be supported on the housing such that, when zero differential pressure can be applied to the diaphragm, the diaphragm can be partially rolled over the electrode projecting portion.

A through hole can be formed in the housing such that the cavity formed between diaphragm and electrode is generally connected to atmosphere.

The pressure sensor system can include a remote interrogation circuit for wirelessly transmitting an electromagnetic signal to the inductor and for analyzing the resonant frequency of the pressure sensor LC (tank) circuit. Obtaining data from the pressure sensor without wires variously reduces the cost of sensor interconnects, makes integration of the sensor into the disposable/commodity part easier and cheaper, improves disposal and/or interchangeability of the parts in the final application and furthermore increases the lifetime of any non-disposable/multiple-use components by removing the need to make and break mechanical electrical connections.

According to another aspect, a pressure sensor has a housing having a bottom wall and at least one side wall defining a cavity. A diaphragm, supported on the side wall(s), separates the cavity from an external pressure region. The diaphragm comprises a conductive material. An electrode can be disposed on the housing wall facing the diaphragm so as to define a capacitor with a gap between at least part of the diaphragm and at least part of the electrode. The electrode can be arranged such that the diaphragm can roll in capacitive contact with the electrode so as to vary the area of contact upon displacement of said diaphragm. An insulating layer can be disposed between the electrode and conductive material of the diaphragm to provide a dielectric layer between the electrode and diaphragm. An inductor coil, formed on the bottom wall of the housing can be electrically connected to the pressure sensing capacitor so as to form an LC tank circuit. The area of contact between diaphragm and electrode with only dielectric between varies as a function of the pressure differential applied to the diaphragm such that the capacitance of the pressure sensing capacitor varies. When an electromagnetic signal can be applied to the pressure sensor, the resonant frequency of said LC tank can be detected to enable determination of changes in said pressure differential.

The bottom wall can comprise an inner region and an outer region surrounding the inner region. The outer region is substantially planar in form and the inner region can be shaped to form a protrusion of curved or mound like shape such that said diaphragm can roll over the inner region upon displacement of said diaphragm. The electrode can be formed as a layer contiguous with the inside of said bottom wall so as to form a rolling capacitive contact.

According to yet another aspect, a method of manufacturing a pressure sensor comprises the steps of providing a housing having a bottom wall and at least one sidewall, the bottom and sidewall(s) forming a cavity, securing a diaphragm in the sidewall(s) so as to separate the cavity from an external pressure region, the diaphragm comprising a conductive material, arranging an electrode on the inside of the bottom wall such that the diaphragm can roll in capacitive contact with the electrode so as to vary said contact area upon displacement of the diaphragm, forming an inductor coil on the bottom wall, forming an electrical interconnect between one end of the inductor coil and the electrode, forming an electrical interconnect between the other end of the inductor coil and the diaphragm.

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

DETAILED DESCRIPTION OF THE INVENTION

Figure 1:
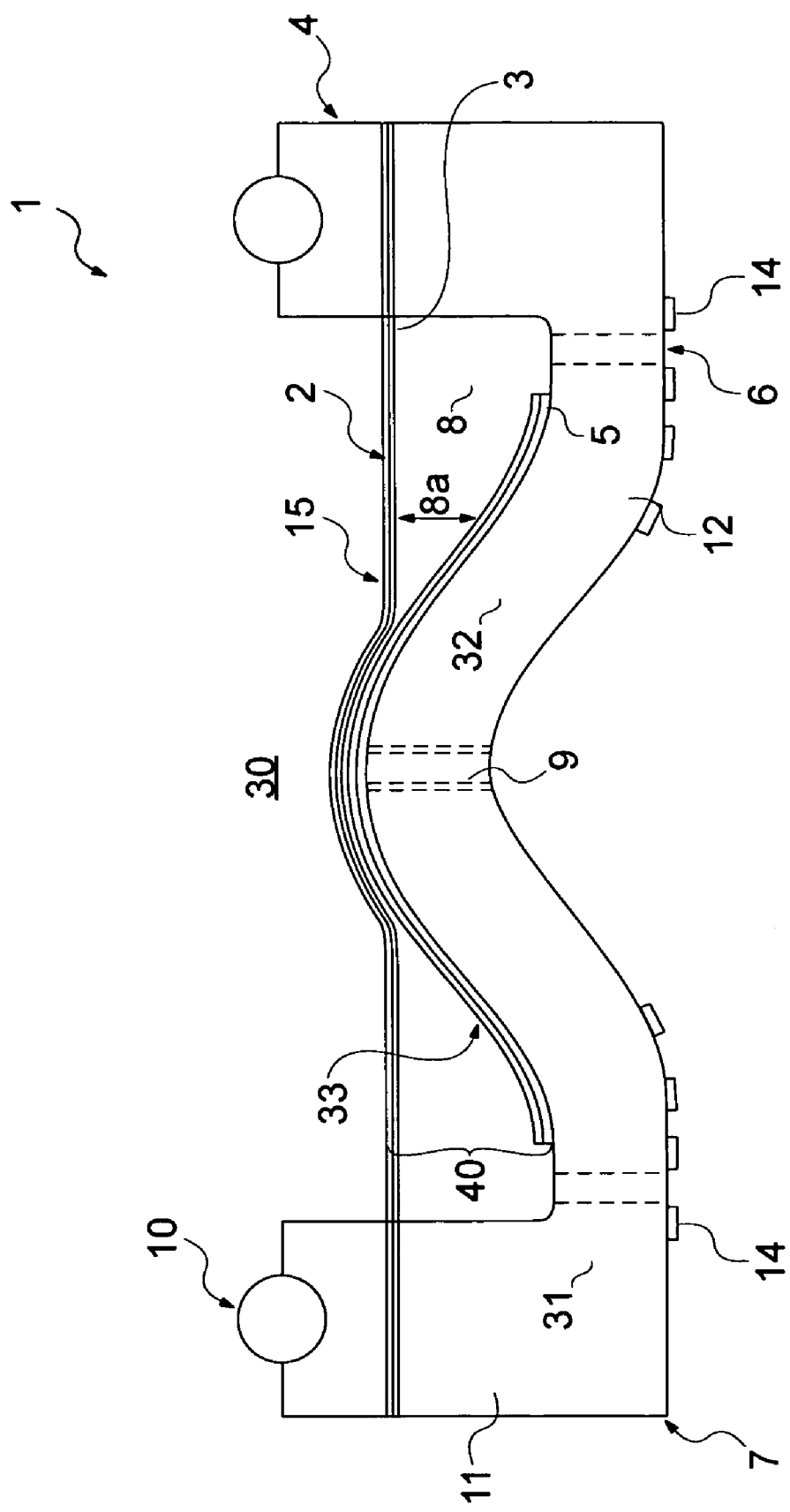
FIG. 1 illustrates a cross-sectional view of the pressure sensor assembly according to a preferred embodiment.

Referring to FIG. 1 of the accompanying drawings, which illustrates a cross-sectional view of a pressure sensor in accordance with an embodiment, the pressure sensor 1 has an annular housing 7 having an annular cavity or recess 8 formed therein and a diaphragm 15, mounted on the housing 7 so as to separate the cavity from an external pressure region 30. An electrode 5 can be also mounted on the housing, inside the cavity 8 and beneath the diaphragm 15, such that a gap 8a is generally formed between outer regions of the diaphragm and electrode. As will be explained in more detail below, the electrode 5 can be arranged relative to the diaphragm 15 such that, upon displacement of the diaphragm, the diaphragm varies the gap 8a by rolling in capacitive contact with the electrode.

The diaphragm 15 and electrode 5 together define a pressure sensing capacitor 40. Capacitance of said capacitor is dominated by area of overlap between diaphragm 15 and electrode 5 with insulating layer 33 sandwiched therebetween. Sensing capacitor 40 can be electrically connected to an inductor 14 to form an LC (tank) resonant circuit. When the gap 8a varies as a function of a pressure differential applied to the diaphragm 15, the capacitance of the pressure sensing capacitor 40 varies, which in turn, varies the resonant frequency of the LC tank. As will be discussed in more detail below, the resonant frequency can be detected by means of an interrogation circuit inductively coupled to the inductor 14 (see FIG. 6).

By forming the pressure sensing capacitor 40 and inductor 14 within the same housing 2, the number of components and manufacturing steps necessary to produce the pressure sensor 1 are reduced enabling a low cost capacitance pressure sensor to be provided.

Those skilled in the art would understand that the illustration of FIG. 1 merely depicts one example of the embodiments and that the embodiments are not limited thereto. For example, the pressure sensor need not have an annular configuration so as to function and can have many other different shapes and forms.

Figure 3:
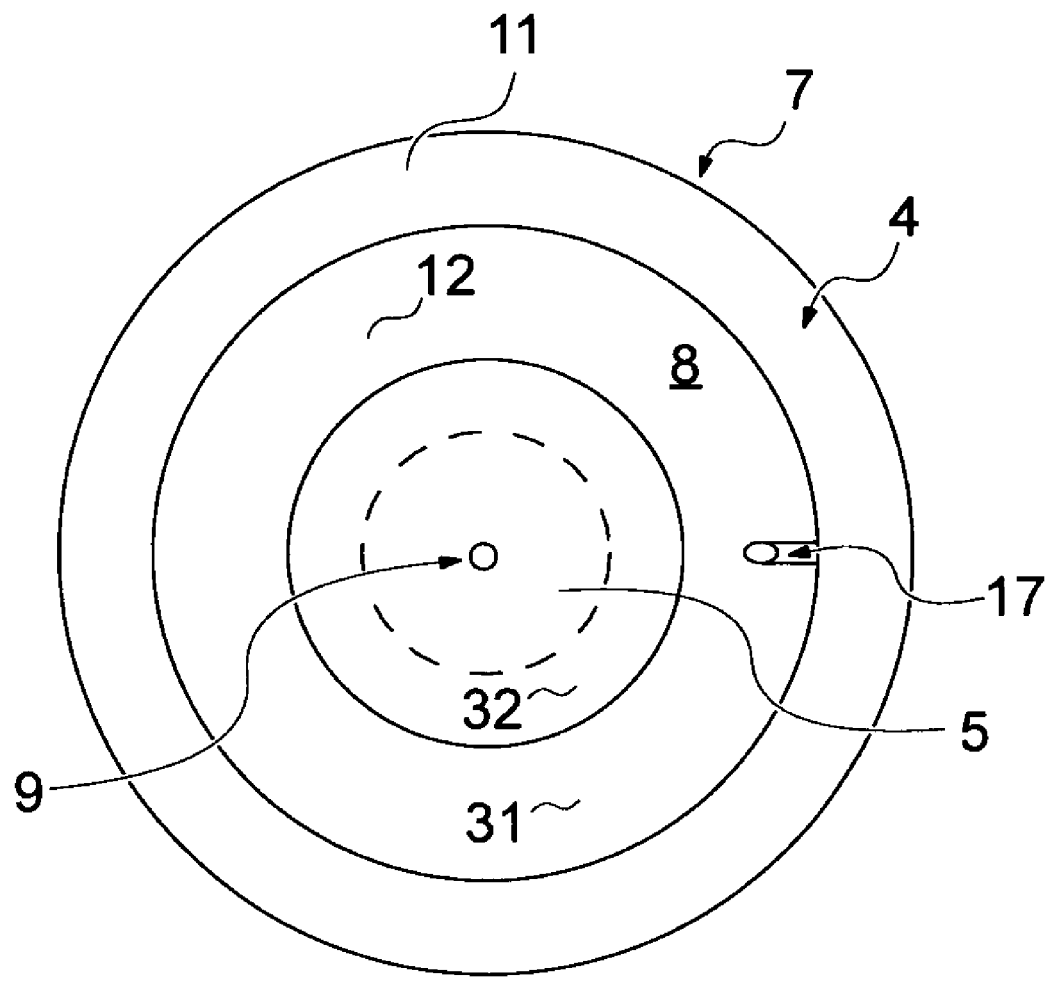
FIG. 3 illustrates a top plan view of the pressure sensor assembly of FIG. 1 with the diaphragm omitted.
Figure 4:
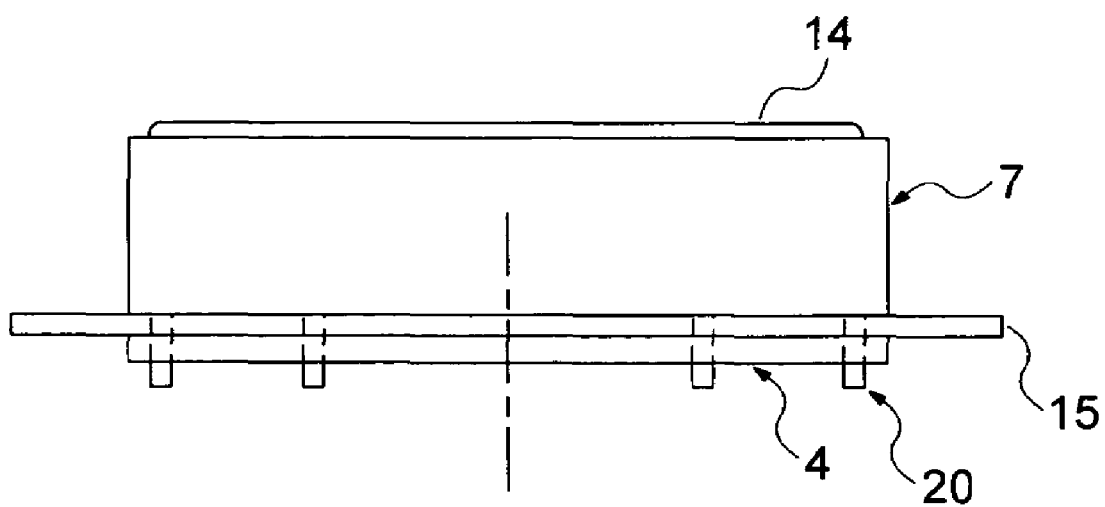
FIG. 4 illustrates a side view of the pressure sensor assembly of FIG. 1 following mounting of the frame on the housing.

Referring to FIG. 1 and FIG. 3, which illustrates a plan view of the top of the pressure sensor of FIG. 1 with the diaphragm omitted, the cavity 8 can be defined by an annular sidewall 11 and a bottom wall 12 of the housing 7. The cavity 8 diameter can be selected to be large enough to give both sufficient capacitance and diaphragm displacement. A through hole 6 connecting the cavity 8 to atmosphere serves as a vent. Preferably, the housing 7 can be configured from polymers suited to injection moulding, for example polycarbonates, polyesters such as PET or nylon and PVC. Particularly suitable for use in pressure sensors for medical applications and other applications in which high stability is required are polymers which remain mechanically and chemically stable when exposed to various media and cleaning/sterilization processes, with glass temperature significantly higher than any subsequent operating/processing temperatures, for example high performance polymers such as liquid crystal polymers, PEEK™, polyetherimide, polysulphone, polyimide, and syndiotactic polystyrene (SPS).

The bottom wall 12 has a substantially planar annular outer region 31 surrounding an inner region 32 which inner region can be shaped to form a protuberance in the form of a mound or hill, having a hemispherical or rounded apex, projecting towards the diaphragm 15 such that the diaphragm can roll over the protuberance upon displacement thereof.

The diaphragm 15 can be formed from a flexible membrane 2, having low modulus of elasticity such as silicone, with a conductive layer 3, such as a metallized layer, formed on the underside of the membrane. The dimensions of the diaphragm for a given material or material combination are selected such that the diaphragm has sufficient flexibility and stiffness to function. For example, for sensor operation in range +1 bar to −1 bar gauge, the diaphragm can have a diameter ranging from 1 mm to 10 cm and a corresponding thickness from 0.5 micron to 1000 microns.

Figure 5:
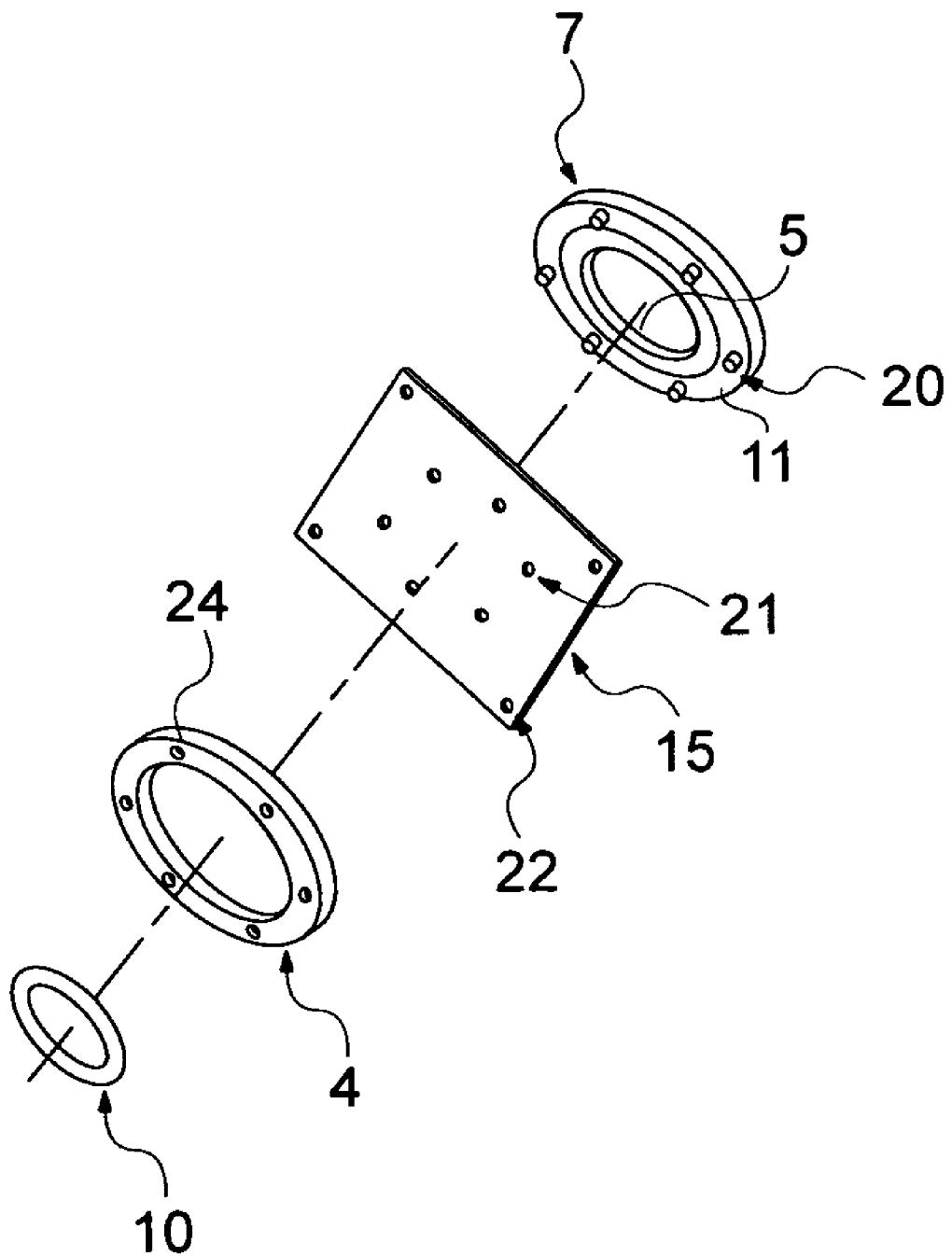
FIG. 5 illustrates an exploded perspective view of the pressure sensor assembly of FIG. 1.

As best shown in FIG. 5, which illustrates an exploded perspective view of the pressure sensor of FIG. 1, diaphragm 15 can be initially formed from a sheet of material having distributed location holes 21 formed therethrough which locate on corresponding locating pins 20 distributed about the upper surface of the annular sidewall 11. A ring or frame 4, also having location holes 24 for locating on corresponding pins 20 can be mounted on the diaphragm and press fitted onto the pins 20 so as secure the diaphragm between the frame and housing. An 'O' ring seal 10, which can be utilized to seal the pressure sensor 1 to a fluid housing or chamber (not shown), is mounted in an annular groove formed in the frame 4.

Other methods of securing said diaphragm and sealing the pressure sensor may of course be utilized, non-limiting examples being the use of adhesive, ultrasonic weld, laser weld and/or use of separate securing clip structures.

A metal layer can be deposited on the inside of the bottom wall 12 so as to form the electrode 5 contiguous with the inside of the bottom wall. The portion of the electrode 5 disposed on the inner region 32 and the diaphragm 15 can define a rolling capacitive contact. An insulating layer 33 can be deposited on the electrode so as to form the dielectric layer between the electrode 5 and diaphragm 15. The insulating layer 33 could equally be disposed on the conductive layer 3 of the diaphragm 15 the insulating material of the diaphragm itself can be utilized as the dielectric between the diaphragm and electrode 5 to achieve the same result.

As shown in FIG. 1, the periphery of the diaphragm 15 can be secured on the annular wall 11 at a position which is generally lower relative to the apex of the electrode projecting portion such that even when a negative differential pressure can be applied to the diaphragm, the central region of the diaphragm maintains contact with the electrode protruding portion. Arranging the diaphragm in this manner ensures that the diaphragm 15 can roll down over the electrode in capacitive contact therewith upon displacement of the diaphragm towards the bottom wall and that the diaphragm 15 can roll up off the electrode 5 in capacitive contact therewith upon displacement of the diaphragm away from the bottom wall. Consequently, the pressure sensing capacitor 40 is capable of having varying capacitance both in response to negative and positive differential pressures applied to the diaphragm.

Rolling contact capacitance between diaphragm 15 and electrode 5 with dielectric 33 between provides a high capacitive change relative to diaphragm displacement. The pressure sensor therefore affords an increased capacitive response for a given diaphragm displacement in comparison to other sensors without a rolling capacitive contact design so that the sensitivity of the pressure sensor can be increased.

Those skilled in the art will understand that other configurations of the diaphragm and/or electrode can be employed to achieve rolling capacitive contact sensing mechanism. For example, the electrode need not be shaped so as to have a hemispherical or rounded apex as in the case in the embodiment shown in FIG. 1. Rolling contact may still be achieved using an electrode having alternative shaped projections, such as conical or cubic. The shape can also vary with height of the projection, so that the gradient varies in such as way as to tailor the relationship between diaphragm displacement and contact area.

All that is required is that a gap is formed between at least part of the diaphragm and at least part of the electrode and that the electrode is configured to project towards the diaphragm to enable the diaphragm to roll over the electrode upon displacement. Furthermore, it is not essential that the diaphragm be in rolling contact with electrode at all times. For example, the diaphragm could be mounted on the housing such that a gap initially exits between the diaphragm and the projecting electrode portion and such that the diaphragm makes subsequent capacitive contact with and rolls over the electrode upon diaphragm displacement.

Figure 2:
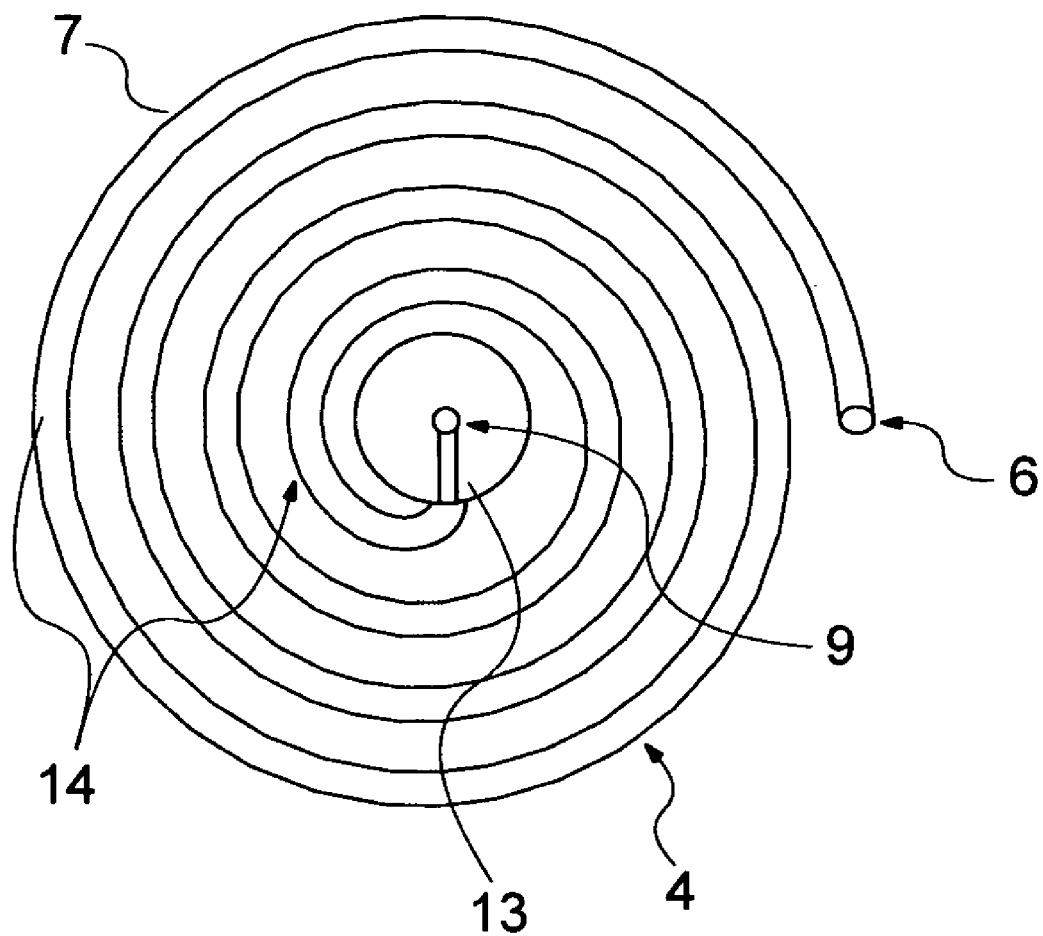
FIG. 2 illustrates a bottom plan view of the pressure sensor assembly of FIG. 1.

Referring to FIG. 2, which illustrates a plan view of the bottom of the pressure sensor of FIG. 1, an inductor coil 14, formed on the outside of the bottom wall 12, is spaced from and electrically coupled to the pressure sensing capacitor 40. The inductor coil 14 is mounted predominantly on the outer region 12 of the bottom wall rather than the projecting inner region 32 so that the coil is located in a plane substantially parallel to the plane in which the diaphragm 15 is located. Utilizing a single layer coil 14 minimizes parastatic capacitance and also reduces the manufacturing steps necessary to produce the sensor and therefore the sensor cost. However, the coil could instead take the form of multiple layers and/or could be embedded in the housing.

A plated through-hole 9, formed about the centre of the bottom wall 12, electrically connects the electrode 5 to a metal trace 13 formed on the outside of the bottom wall, which, in turn, connects to the inner end of the coil 14. As best shown in FIGS. 1 & 3, the outer end of the coil is electrically connected to the periphery of the diaphragm 15 by means of metal plating in the through-hole 6 and a trace 17 electrically connecting the through-hole 6 to the periphery of the conductive layer 3 of the diaphragm.

If required, a protective region (not shown) for additional media isolation can be formed above the diaphragm 15 to isolate the diaphragm from the media. A thin coating such as for example, parylene or PTFE (Teflon) can be formed on the diaphragm for this purpose.

Figure 6:
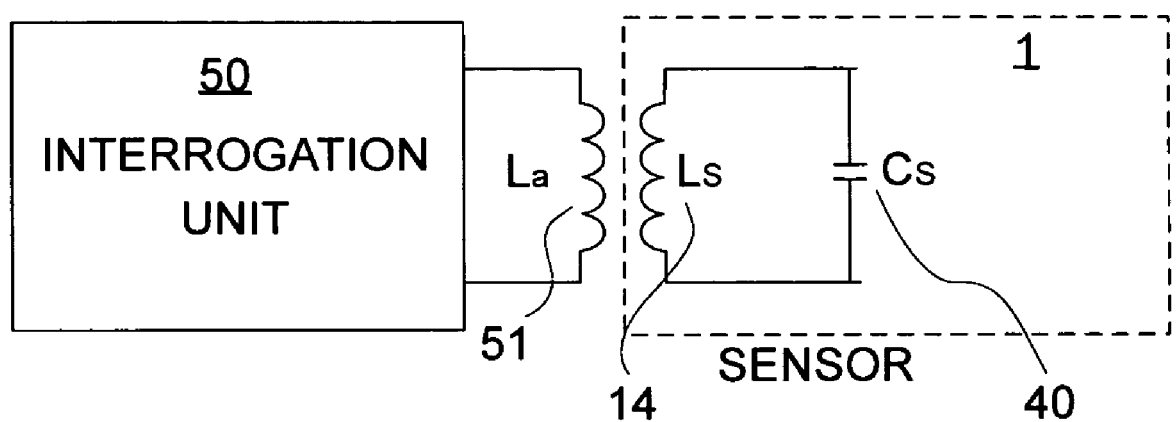
FIG. 6 illustrates an equivalent electrical circuit of the pressure sensor of FIG. 1. inductively coupled to the antenna coil of an interrogation unit.

A method of operating a pressure sensor system including the pressure sensor 1 and an interrogation unit 50 for remotely measuring the differential pressure between the external median 30 and cavity 8 will now be described with reference to FIGS. 1 & 6. When the pressure sensor 1 is located in its operating position, an interrogation electromagnetic signal is inductively coupled from a coil (loop) antenna 51 of the interrogation unit 50 to the pressure sensor inductor coil 15, preferably perpendicular to the plane of the coil so as to induce a current therein.

A change in the differential pressure between the cavity 8 and external median 30 deflects the diaphragm 15 causing the diaphragm to roll in capacitive contact with electrode 5 varying the gap 8a therefore changing the capacitance of the pressure sensing capacitor 40. This change in capacitance causes a corresponding change in the resonant frequency of the LC tank of the pressure sensor 1. The coupling impedance of the sensor LC circuit to coil antenna 51 is analyzed by the interrogation unit to remotely detect the resonant frequency of the sensor LC circuit. One non-limiting example of such an interrogation unit would employ a grid-dip oscillator circuit to enable determination of the sensor resonant frequency.

Obtaining data from the pressure sensor without wires variously reduces the cost of the sensor, makes integration of the sensor into the disposable/commodity part easier and cheaper, improves disposal and/or interchangeability of the parts in the final application and furthermore increases the lifetime of any non-disposable/multiple-use components by removing the need to make and break mechanical electrical connections.

The description as set forth is not intended to be exhaustive or to limit the scope of the invention. Many modifications and variations are possible in light of the above teaching without departing from the scope of the following claims. It is contemplated that the use of the present invention can involve components having different characteristics. It is intended that the scope of the present invention be defined by the claims appended hereto, giving full cognizance to equivalents in all respects.

The embodiments and examples set forth herein are presented to best explain the present invention and its practical application and to thereby enable those skilled in the art to make and utilize the invention. Those skilled in the art, however, will recognize that the foregoing description and examples have been presented for the purpose of illustration and example only. Other variations and modifications of the present invention will be apparent to those of skill in the art, and it is the intent of the appended claims that such variations and modifications be covered.

What is claimed is:

1. A pressure sensor, comprising:
   a pressure sensing capacitor comprising:
   a housing defining a cavity,
   a diaphragm, supported on said housing and separating said cavity from an external pressure region, said diaphragm comprising a conductive material,
   an electrode disposed on said housing inside said cavity and facing said diaphragm so as to define a gap between at least part of said diaphragm and at least part of said electrode, wherein said electrode is arranged such that said diaphragm can roll against said electrode in capacitive contact therewith so as to vary the contact area upon displacement of said diaphragm;
   an insulating layer disposed between said electrode and said diaphragm to provide a dielectric layer between said electrode and said diaphragm, and
   an inductor, formed on said housing, electrically connected to said pressure sensing capacitor so as to form an LC tank circuit,
   wherein said gap varies as a function of a pressure differential applied to said diaphragm such that the capacitance of said pressure sensing capacitor varies, and
   whereby, an electromagnetic signal can be applied to the pressure sensor to detect the resonant frequency of said LC tank to determine said pressure differential.

2. The system of claim 1, wherein said electrode is shaped such that a portion of said electrode projects towards said diaphragm, said diaphragm rolling against said projecting portion in capacitance therewith upon displacement of the diaphragm.

3. The system of claim 2, wherein said projecting portion has a curved or rounded shape apex.

4. The system of claim 1, wherein said electrode has an inner region and an outer region surrounding said inner region, said outer region being substantially planar and said inner region projecting towards said diaphragm such that said diaphragm can roll against said inner region in capacitive contact therewith.

5. The system of claim 1, wherein the inductor comprises an inductor coil disposed on said housing.

6. The system of claim 5, further comprising first and second metal interconnects formed on or in said housing for electrically connecting said inductor coil to said pressure sensing capacitor, said first metal interconnect connecting one end of said coil to said electrode and a second metal interconnect connecting the other end of said coil to said diaphragm.

7. The system of claim 1, wherein said housing is formed with a portion projecting towards said diaphragm, said electrode
   being disposed contiguous with said housing projecting portion such that said electrode-projects towards said diaphragm.

8. The system of claim 1, wherein said diaphragm is supported on said housing such that, when zero differential pressure is applied to said diaphragm, said diaphragm is partially rolled over said electrode projecting portion.

9. The system of claim 1, including an interrogation circuit for transmitting an electromagnetic signal to said inductor and for analyzing the resonant frequency of said pressure sensor LC (tank) circuit.

10. The system of claim 1, wherein said diaphragm comprises a polymer with low modulus of elasticity having a metallized layer formed thereon.

11. A pressure sensor, comprising:
    a pressure sensing capacitor comprising:
    a housing having a bottom wall and at least one side wall defining a cavity,
    a diaphragm, supported on the said side wall(s), separating said cavity from an external pressure region, said diaphragm comprising a conductive material,
    an electrode disposed inside said cavity, adjacent said diaphragm, so as to define a gap between at least part of said diaphragm and at least part of said electrode, wherein said electrode is shaped to form a protuberance or protrusion such that said diaphragm can roll against said protuberance or protrusion in capacitive contact with said electrode upon displacement of said diaphragm;
    an insulating layer disposed between said electrode and said diaphragm to provide a dielectric layer between said electrode and said conductive material of said diaphragm, and
    an inductor coil, formed on or in the bottom wall of said housing, electrically connected to said pressure sensing capacitor so as to form an LC tank circuit,
    wherein said gap varies as a function of pressure differential applied to said diaphragm such that the capacitance of said pressure sensing capacitor varies, and
    whereby, when an electromagnetic signal is applied to the pressure sensor, changes in resonant frequency of said LC tank are detectable in order to determine said pressure differential.

12. The system of claim 11, wherein said bottom wall comprises an inner region and an outer region surrounding said inner region, said outer region being substantially planar in form and said inner region being shaped also to form a protuberance or protrusion, and wherein said electrode is formed as a layer contiguous with the inside of said bottom wall such that said electrode is shaped to form said electrode protuberance or protrusion.

13. The system of claim 12, wherein the apex of said protuberance or protrusion has a hemispherical or rounded shape.

14. The system of claim 11, wherein said inductor coil is disposed on the outside of said bottom wall about said outer region in a plane substantially parallel to the plane of said diaphragm.

15. The system of claim 14, further comprising first and second metal interconnects formed on or in said housing, said first metal interconnect connecting the inner end of said coil to said electrode via a through hole located about the centre of the bottom wall inner region and said second metal interconnect connecting the outer end of said coil to said diaphragm via a through-hole located about said bottom wall outer region.

16. The system of claim 11, further comprising locating pins distributed on said side wall(s), said diaphragm having corresponding location holes at the periphery thereof for locating on said sidewall locating pins to locate said diaphragm on said housing.

17. The system of claim 16, further comprising a frame for attaching on the periphery of said metal sheet, said frame having corresponding locating holes for locating on said housing locating pins to securely fix said diaphragm between said frame and said sidewall(s) of said housing.

18. A method of manufacturing a pressure sensor comprising the steps of providing a housing having a bottom wall and at least one sidewall, said bottom and sidewall(s) forming a cavity, forming a diaphragm on said sidewall(s) so as to separate said cavity from an external pressure region, said diaphragm comprising a conductive material, arranging an electrode to form a protuberance or protrusion inside said cavity such that said diaphragm can roll against said protuberance or protrusion in capacitive contact with said electrode so as to vary said gap upon displacement of said diaphragm, forming an insulating layer between said conductive material of said diaphragm and said electrode, forming an inductor coil on the bottom wall, forming an electrical interconnect between one end of said inductor coil and said electrode, forming an electrical interconnect between the other end of said inductor coil and said diaphragm.

19. The method of claim 18, further comprising shaping said bottom wall of said housing to form a protuberance or protrusion, and wherein arranging said electrode in said cavity comprises forming a conductive layer contiguous with the inside of said bottom wall.

* * * * *